United States Patent [19]
Farrell

[11] Patent Number: 5,624,919
[45] Date of Patent: Apr. 29, 1997

[54] TRANS PLATINUM (IV) COMPLEXES

[75] Inventor: Nicholas Farrell, Richmond, Va.

[73] Assignee: The University of Vermont and State Agricultural College, Burlington, Vt.

[21] Appl. No.: 304,837

[22] Filed: Sep. 13, 1994

Related U.S. Application Data

[63] Continuation-in-part of Ser. No. 120,433, Sep. 14, 1993, abandoned.

[51] Int. Cl.$^6$ .................... C07F 15/00; A61K 31/555
[52] U.S. Cl. .................... 514/184; 514/185; 514/186; 514/187; 544/225; 546/10; 548/101; 548/108; 548/109; 548/402
[58] Field of Search .................... 514/184, 185–188; 544/225; 546/2, 10, 12; 548/101, 108, 109, 402

[56] References Cited

FOREIGN PATENT DOCUMENTS

| | | |
|---|---|---|
| 328274 | 8/1989 | European Pat. Off. . |
| 503830 | 9/1992 | European Pat. Off. . |
| 2122194 | 1/1984 | United Kingdom . |

OTHER PUBLICATIONS

Massacesi, G.T. Inorg Biochem. 29, 95(1987).

Hazarika, Polyhedron 3, 121–124 (1984).

Singhal, T. Indian Chem Soc 18A, p. 449 (1979).

Kukushkin, Zh. Neorg. Khim. 26(8), 2190 (1981).

Floris, Trans. Met. Chem 17, 145–146(1992).

Primary Examiner—Mark L. Berch
Attorney, Agent, or Firm—Burns, Doane, Swecker & Mathis, L.L.P.

[57] ABSTRACT

Novel trans-platinum IV complexes which contain heterocycle ligands such as quinoline or isoquinoline, anionic ligands such as halide or sulfate, and which optionally may contain ammonia, or a primary or secondary amine are provided. These complexes have application as pharmaceuticals, in particular as anti-tumor agents.

17 Claims, No Drawings

TRANS PLATINUM (IV) COMPLEXES

This application is a continuation-in-part of U.S. application Ser. No. 08/120,433, filed Sep. 14, 1993, ABN which is herein incorporated by reference in its entirety.

FIELD OF THE INVENTION

The invention relates to novel trans platinum(IV) complexes, methods for their preparation, and methods for their use as pharmacological agents, in particular, for treatment of cancer.

BACKGROUND OF THE INVENTION

The clinical use of platinum complexes such as cisplatin and carboplatin in cancer chemotherapy is well established in the art. A number of platinum complexes, such as Platinol, a registered trademark of cisplatin manufactured by Bristol Myers, Co., are used to treat testicular, ovarian, head and neck, and small-cell lung carcinomas. However, treatment with cisplatin may result in severe nephrotoxicity. A further clinical disadvantage is the problem of acquired drug resistance resulting in the tumor becoming refractory to treatment by the agent.

To overcome the nephrotoxic effects of cisplatin, a second-generation analog, carboplatin, was developed. Paraplatin is a registered trademark for carboplatin manufactured by Bristol-Myers, Co. Carboplatin, or $[Pt(NH_3)_2(CBDCA)]$ (where CBDCA is 1,1'cyclobutanedicarboxylate), is effective against the same spectrum of carcinomas as cisplatin, but exhibits a marked reduction in the nephrotoxic effects.

A number of different platinum compounds have been developed in an attempt to treat different tumors or carcinomas. For instance, U.S. Pat. No. 4,225,529 discloses the use of a cis coordination compound of platinum having four ligands which are selected from the group consisting of halides, sulphates, phosphates, nitrates, carboxylates, and same or different straight-chain amines which are coordinated to the platinum atom through their nitrogen atoms. These complexes are used for treating L-1210 leukemia in mice.

Also, U.S. Pat. Nos. 4,250,189, 4,553,502, and 4,565,884 relate to various Pt(II) and Pt(IV) complexes having antitumor activity. These bis(platinum) complexes are linked with a carboxylate linkage such that upon administration of these complexes to the patient, the complexes undergo rapid hydrolysis to produce two cis monoplatinum moieties which are then delivered to the active site.

Additionally, PCT WO 88/00947, which corresponds to U.S. Pat. No. 4,797,393, discloses a bis(platinum) complex which is delivered intact to the active site. This bis (platinum) complex has a bridging diamine or polyamine ligand and has primary or secondary amines or pyridine type nitrogens attached to the platinum complex, as well as two different or identical ligands which may be a halide, sulphate, phosphate, nitrate, carboxylate, substituted carboxylate or dicarboxylate. PCT WO 88/00947 also relates to bis(platinum) complexes wherein the platinum moieties are linked by a diamine bridging agent, and wherein the platinum moieties are attached to ionic and neutral groups such that the net charge on the two platinum coordination spheres is 2+ or 1+.

However, critical problems still exist which limit the effective use of platinum complexes as therapeutics, most especially their narrow spectrum of activity against different tumors and the development of tumor cells which are resistant to the cytotoxic effects of cisplatin. (Loehrer et al., *Ann. Intern. Med.*, (1984), 100, 704–711). For a general review relating to available platinum analogs, see, Christian, Michael, *Seminars in Oncology*, 1992, 19, 720–733.

It is generally believed that platinum complexes such as cisplatin manifest their biological activity through covalent interaction with DNA. In particular, cisplatin induces the formation of a range of adducts on DNA including monodentate adducts, bidentate adducts, such as GG or AG, and GNG intrastrand crosslinks. (Reedijk et al., *Structure and Bonding*, (1987), 67, 53–89). To a lesser extent, cisplatin also results in interstrand GG crosslinks and DNA-protein crosslinks. (Rahmouni et al., *Biochemistry*, (1987), 26, 7229–7234). These DNA lesions result in conformational changes which are reflected in bending and local unwinding of the DNA. These DNA lesions have been reported to inhibit the activity of various DNA polymerases. (Vallan et al., *Nucl. Acids Res.*, (1988), 16, 4407–4418; Pinto et al., *Proc. Natl. Acad. Sci*, (1985), 82, 4616–4619; and Gralla et al., *Cancer Res.*, (1987), 47, 5092–5096). The interstrand crosslink between two neighboring guanine bases has also been shown to inhibit RNA polymerase function. (Lemaire et al., *Proc. Natl. Acad. Sci.*, (1991), 88, 1982–1985). Accordingly, the cytotoxic effects of cisplatin are most likely attributable to the combined effects of these separate DNA lesions, rather than the result of any one specific lesion event.

Mono(platinum) and bis(platinum) complexes respectively containing one or two platinum atoms are known in the art. (See, e.g., U.S. Pat. Nos. 4,225,529, 4,250,189, 4,533,502, 4,565,884, 4,571,335 and 4,797,393). For example, mono(platinum) complexes include monomeric chloramine square-planar Pt(II) compounds which are four coordinate. The relative number of chloride and ammonia groups in such compounds may vary and these compounds may therefore be described by the general formula:

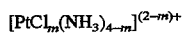

Thus, the structure of these compounds may vary from $[Pt(NH_3)_4]^{2+}$ where m=0 to $PtCl_4^{2-}$ where m=4. Since Cl is more substitution labile in comparison to ammonia, the complexes $[PtCl_2(NH_3)_2]$ and $[PtCl(NH_3)_3]Cl$ are considered bifunctional and monofunctional respectively, wherein the bi and mono prefixes refer to the number of leaving ligands. The charge of the complex is determined by the fact that the Pt(II) cation has a formal charge of +2 and thus requires a negative charge of −2 for charge neutralization. For example, when m=0, neutralization is provided by the presence of two anions, such as chloride anions.

Coordinate bond formation results in electron pairing in the Pt-Cl bond. However, since the ammonia ligand is considered to be neutral, the bonding may be described as electron-pair donation from $NH_3$ to the empty orbitals on the Pt(II) atom. Thus, no electron sharing between the Pt and $NH_3$ group takes place. Because of this absence of electron sharing, the number of neutral ligands does not affect the overall charge in the Pt coordination sphere. Thus, $[Pt(NH_3)_4]^{2+}$ is formally a 2+ cation requiring a non-coordinating anion or anions, or counter-anions, having a net negative charge of 2− for neutralization of the complex. For example, neutralization can be provided by two mononegatively charged anions (e.g., $NO_3^-$, $Cl^-$, $PF_6^-$, $BF_4^-$, and monocarboxylates having the general formula $RCOO^-$) or a single dinegatively charged anion (e.g., $SO_4^{2-}$, dicarboxylates having the general formula $(RCOO)_2^{2-}$). Therefore, $[PtCl_2$ (NH$_3$)$_2$] is a neutral complex. Moreover, in some cases, Pt(II) anions may serve as counter-anions. An example is the well known Magnus salt [Pt(NH$_3$)$_4$]$^{2+}$[PtCl$_4$]$^{2-}$.

It is noted that anionic ligands such as Cl$^-$, may be either coordinately bound (i.e., forming a Pt-Cl bond) or may act as a counter-anion without any need for covalent bond formation. The exact form that anions such as Cl$^-$ are present in a given platinum complex depends both on theoretical considerations (kinetic vs. thermodynamic effects) and the actual synthetic procedures utilized to make the complex (e.g., the extent of reaction, acidity, concentration of the particular anion, such as the concentration Cl$^-$ which is contained in the reaction mixture). These considerations are applicable to other anionic and neutral ligands as well.

The fact that the overall charge of monoplatinum complexes depends on the relative number of neutral and anionic ligands which are bound to the Pt(II) metal, e.g., NH$_3$ and Cl$^-$ ligands, is also applicable for polynuclear complexes (which contain more than one Pt(II) coordinate spheres), and for Pt(IV) containing complexes wherein the oxidation state of the platinum moiety is 4+. For example, dinuclear complexes where two equivalent Pt(II) coordination spheres are linked by a diamine bridging agent may be represented by the general formula [{PtCl$_m$(NH$_3$)$_{3-m}$}$_2$(diamine)]$^{2(2-m)+}$. Thus, when m=2, and two bifunctional coordination spheres are present, the compound is neutral. In contrast, when m=1, only monofunctional coordination spheres are present and the Pt moiety has a formal charge of 2+ which must be counterbalanced by one or more counter-anions having a net charge of 2−.

A more widespread use of platinum complexes in cancer treatment is limited by factors such as inherent resistance, which limits activity against many common human tumors and the phenomenon of acquired drug resistance which results in reduced efficacy after repeated treatments. Therefore, considerable effort has been undertaken in the search for new platinum compounds with improved properties.

The structure activity relationships originally delineated for platinum complexes stressed the necessity for the cis-[PtX$_2$(amine)$_2$] structure, where X is a leaving group, such as chloride and the amine is ammonia or a primary monodentate or bidentate amine. The trans isomer of cisplatin, trans-[PtCl$_2$(NH$_3$)] and in general the trans platinum complexes are considered inactive (Cleare in Coordination Chemistry Reviews, 12, 349, 1974) and the same author made clear that above structure activity relationships were valid both for Pt(II) and Pt(IV) complexes (Cleare; "Structure activity relationship of antitumor agents" Ed D. N. Reinhardt et al., Martinus Nijhof Publishers, The Hague (1983)). Recently some trans-platinum (IV) complexes beating as inert ligands primary or secondary amines, have been disclosed in EP 0 503 830 A 1 as useful in the treatment of experimental tumors in animals. Nevertheless, the search for improved platinum complexes continues.

OBJECTS AND SUMMARY OF THE INVENTION

As discussed supra, the structure activity relationships originally delineated for platinum complexes stressed the necessity for the cis- structure for cancer therapeutic agents. In contrast, the present invention describes the synthesis of trans platinum(IV) complexes which differ from the prior art compounds for having at least one heterocyclic planar ligand. It has been surprisingly found that the compounds of the invention exhibit an enhanced cytotoxic activity as compared to currently available platinum complexes.

In its broadest aspect, it is an object of this invention to provide trans platinum(IV) complexes containing at least one heterocyclic planar ligand.

It is a further object of the invention to provide pharmaceutical compositions containing trans platinum(IV) complexes containing at least one heterocyclic planar ligand.

It is another object of the invention to provide methods for synthesizing trans platinum(IV) complexes containing at least one heterocyclic planar ligand.

It is a specific object of the invention to provide trans platinum(IV) complexes of formula I:

wherein A is a nitrogen heterocyclic unsaturated ligand and B is a nitrogen heterocyclic ligand, ammonia, or a primary or secondary amine, with the proviso that A and B are not pyridine; X and Y, which are the same or different, are an anionic ligand, such as halide, sulfate, nitrate, hydroxy, carboxylate, substituted carboxylate or pseudohalogen; and Z is halide, hydroxyl, or —OCO—R, —OC(O)OR, or —OSO$_2$—R, wherein R is H, linear or branched C$_1$-C$_8$ alkyl, C$_3$-C$_6$ cycloalkyl, phenyl, substituted phenyl, or C$_7$-C$_{10}$ aralkyl; or is a sulphoxide group of formula R'R"SO, wherein R' is linear or branched C$_1$-C$_8$ alkyl and R" is: linear or branched C$_1$-C$_8$ alkyl; phenyl unsubstituted or substituted by one or two halogens such as chloride, bromide, fluoride and the like, or mono and dimethoxy substituted phenyl; C$_7$-C$_{10}$ aralkyl, such as benzyl, phenylethyl, phenylpropyl and the like.

With the term "trans platinum (IV) complexes" is intended platinum (IV) complexes of formula (I) in which the planar ligands A and B are in trans with respect to the platinum atom.

It is another specific object of the invention to provide pharmaceutical compositions containing the trans platinum (IV) complex of formula (I).

It is a further object of the invention to provide a method of use of trans platinum(IV) complexes of formula (I) for therapeutic use, e.g., for treatment of tumors or parasitic conditions.

It is still another specific object of the invention to provide a method for synthesizing trans platinum(IV) complexes of the formula (I).

The subject trans platinum(IV) complexes, by virtue of their containing at least one heterocyclic planar ligand, provide for enhanced cytotoxic activity relative to currently available trans platinum(IV) complexes.

DESCRIPTION OF PREFERRED EMBODIMENTS OF THE INVENTION

The present invention provides a novel class of trans platinum(IV) complexes which exhibit enhanced cytotoxic activity as compared to currently available platinum complexes. In particular, the present invention relates to novel trans platinum(IV) complexes bearing heterocyclic planar ligands as chemotherapeutic agents. Surprisingly, an important feature for the effectiveness of trans platinum(IV) complexes in vivo is the presence of at least one heterocyclic planar ligand.

The compounds of the present invention are those of formula I

wherein A is a nitrogen heterocyclic unsaturated ligand and B is a heterocyclic ligand, ammonia, or a primary or secondary amine, with the proviso that A and B are not pyridine; X and Y, which are the same or different, are an anionic ligand, such as halide, sulfate, nitrate, hydroxy, carboxylate, substituted carboxylate or pseudohalogen; and Z is halide, hydroxyl, or —OCO—R, —OC(O)OR, or —OSO$_2$—R, wherein R is H, linear or branched $C_1$-$C_8$ alkyl, $C_3$-$C_6$ cycloalkyl, phenyl, substituted phenyl, or $C_7$-$C_{10}$ aralkyl; or is a sulphoxide group of formula R'R"SO, wherein R' is linear or branched $C_1$-$C_8$ alkyl and R" is: linear or branched $C_1$-$C_8$ alkyl; phenyl unsubstituted or substituted by one or two halogens such as chloride, bromide, fluoride and the like, or mono and dimethoxy substituted phenyl; $C_7$-$C_{10}$ aralkyl, such as benzyl, phenylethyl, phenylpropyl and the like.

Nitrogen heterocyclic ligands which are suitable as planar ligands in the practice of the present invention preferably include quinoline, pyrroline, isoquinoline, imidazole, benzimidazole, indazole, benzothiazole, thiazole, isothiazole, benzisotriazole, indole, pyrazole, 1,2,3-triazole, pyrazine, isoindole, indoline, cinnoline, quinazoline, 1-8-naphthyridine, acridine, substituted quinoline, substituted isoquinoline, thiazole, and the like, most preferably pyrroline and quinoline.

The primary amines preferably include alkyl amines of the formula NH$_2$—R$_1$, where R$_1$ is linear or branched $C_1$-$C_8$ alkyl, preferably methyl, ethyl, n-propyl, isopropyl, n-butyl, sec-butyl, tert-butyl, n-pentyl, n-hexyl, n-octyl, and the like, and where R$_1$ is $C_3$-$C_6$ cycloalkyl, preferably cyclopropyl, cyclobutyl, cyclopentyl, cyclohexyl, and the like.

The secondary amines preferably include alkyl amines of formula NH(R$_1$)$_2$, where R$_1$ is H or linear or branched $C_1$-$C_8$ alkyl, preferably methyl, ethyl, n-propyl, isopropyl, n-butyl, sec-butyl, tert-butyl, n-pentyl, n-hexyl, n-octyl, and the like; and most preferably include NH$_3$.

Suitable Z groups include —OCO—R, —OC(O)OR, and —OSO$_2$—R, wherein R is linear or branched $C_1$-$C_8$ alkyl, preferably methyl, ethyl, n-propyl, isopropyl, n-butyl, sec-butyl, tert-butyl, n-pentyl, n-hexyl, n-octyl, and the like. Suitable Z groups also include —OCO—R, —OC(O)OR, and —OSO$_2$—R, wherein R is $C_3$-$C_6$ cycloalkyl, preferably cyclopropyl, cyclobutyl, cyclopentyl, cyclohexyl, and the like. Suitable Z groups further include —OCO—R, —OC(O)OR, and —OSO$_2$—R, wherein R is substituted phenyl, preferably ortho, meta and para tolyl, and the like; phenyl ring substituted with one or two halogens such as chloride, bromide, fluoride, and the like; or mono and dimethoxy substituted phenyl. Suitable Z groups further include —OCO—R, —OC(O)OR, and —OSO$_2$—R, wherein R is $C_7$-$C_{10}$ aralkyl, preferably phenylmethyl, phenylethyl, phenylpropyl, and the like. Suitable Z groups further include dimethylsulphoxide, methyl, benzylsulphoxide or methyl, phenylsulphoxide groups.

Examples of anionic ligands X and Y also include halides, such as Cl$^-$, Br$^-$, I$^-$, and the like and pseudohalides. Pseudohalides are substances containing two or more electronegative atoms, which in the free state, resemble the halogens. These pseudohalogens give rise to anions which resemble the halide ions in behaviour. Pseudohalides (wherein the definition for "pseudohalide" as set forth on page 560 of "Advanced Inorganic Chemistry" by Cotton and Wilkinson, 1966, and PCT/US87/01738 page 5, lines 20–26, is incorporated by reference herein) suitable for use in the (platinum) (IV) complexes of the present invention include SCN$^-$, CN$^-$, OCN$^-$, NO$_3^-$, carboxylates, monovalent anions such as PF$_6^-$, BF$_4^-$, anionic ligands, divalent anions such as SO$_4^{-2}$, and the like.

More particularly, the trans platinum(IV) complexes of the present invention include:

trans, trans, trans-[PtCl$_2$(OH)$_2$(NH$_3$)L], wherein L=quinoline, isoquinoline, thiazole and benzothiazole;

mer, trans-[PtCl$_3$(OH)(NH$_3$)(quinoline)];

trans-[PtCl$_4$(NH$_3$)L], wherein L=quinoline, isoquinoline, thiazole, and benzothiazole;

trans-[PtCl$_2$(OOCCH$_3$)$_2$(NH$_3$)(quinoline)]; and trans-[PtCl$_3$(OH)(R'R"SO)quinoline] wherein R' is methyl and R" is methyl, benzyl or phenyl.

The trans platinum(IV) complexes of the present invention are intended for use in pharmaceutical compositions. It has been surprisingly found that the compounds of the invention exhibit an enhanced cytotoxic activity as compared to currently available trans platinum complexes. The subject complexes are useful for treatment of the identical diseases and conditions for which cisplatin is used. This includes the treatment of tumors, radiation sensitization or potentiation (Douple et al, *Cisplatin Current Status and Developments*, Eds. A. W. Prestayk et al, Academic Press, 125 (1980); Douple et al, *Platinum Metals Res.*, (1985), 29, 118) and treatment of parasitic diseases such as sleeping sickness (Farrell et al, *Biochem. Pharmacol.*, 1984, 33, 961). The complexes of the present invention will preferably be administered at the same dosage levels of cisplatin, while taking into account the LD$_{50}$ value of the particular trans platinum(IV) complex. Generally, the trans platinum(IV) complex will be combined with a pharmaceutically acceptable carrier. For example, the complex and carrier may be formulated for parenteral or oral administration by methods well known in the art. For instance, see *Remington's Pharmaceutical Sciences* for suitable pharmaceutically acceptable carriers and formulation methods.

The subject platinum(IV) complexes of the present invention are useful in the treatment of cancer, parasitic disorders and other conditions where platinum complexes as indicated above are known to be useful. The therapeutic efficacy of a particular trans platinum(IV) complex will be evaluated by standard methods. For example, the cytotoxic activity of a particular trans platinum(IV) complex may be evaluated in vitro based on its cytotoxicity against L1210 cancer cells, P388 cancer cells, or L1210 or P388 cancer cells resistant to cisplatin. The L1210 assay, in particular, is an accepted method for screening platinum complexes for therapeutic activity.

Those trans platinum(IV) complexes which exhibit cytotoxic activity, e.g., against L1210 cells, will then be tested in vivo in animals, e.g., nude mice containing implanted human tumors. Those trans platinum(IV) complexes which exhibit in vivo activity without substantial adverse effects (e.g., nephrotoxicity) would be then tested clinically in humans.

In order to fully illustrate the present invention and the advantages thereof, the following specific examples are given, it being understood that these examples are intended only to be illustrative without serving as a limitation on the scope of the present invention.

EXAMPLE 1

Complexes 1) trans-[PtCl$_2$(thiazole)$_2$] and [Pt(thiazole)$_4$]Cl$_2$, 2) trans-[PtCl$_2$(N-methylimidazole)$_2$], and 3) trans-[PtCl$_2$(R'R"SO)(quinoline)]; wherein R"=methyl, R"=methyl, benzyl, and phenyl.

The above-identified complexes have been prepared by previously published methods including:

(a) Van Beusichem, M., and Farrell, N. "Activation of the Trans Geometry in Platinum Antitumor Complexes. Synthesis, Characterization, and Biological Activity of Complexes with the Planar Ligands Pyridine, N-Methylimidazole, Thiazole, and Quinoline. Crystal and Molecular Structure of trans-Dichlorobis(thiazole)platinum (II)." *Inorg. Chem.*, (1992), 31, 634–639.

(b) Kaufman, G. B. "cis- and trans-Dichloro(dipyridine) platinum(II)." *Inorg. Synth.*, (1963), 7, 249–253.

(c) Van Kralingen, C. G., de Ridder, J. K., Reedijk, J. "Coordination Compounds of Pt(II) and Pd(II) with Imidazole as a Ligand. New Synthetic Procedures and Characterization." *Inorg. Chim, Acta*, (1979), 36, 69–77.

(d) Graves, B. J., Hodgson, D. J., Van Kralingen, C. G., Reedijk, J. "Synthesis and Structural Characterization of cis-Dichlorobis(N-methylimidazole)platinum(II) and cis-Dibromobis(N-methylimidazole)platinum(II)." *Inorg. Chem.*, (1978), 17, 3007–3011.

EXAMPLE 2

Preparation of Trans-[PtCl$_2$(NH$_3$)L]; wherein L= Quinoline and Isoquinoline

The following reaction scheme was used:

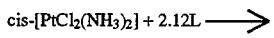

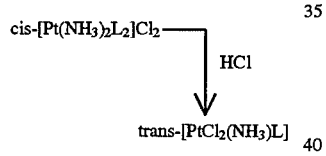

These complexes were prepared by a modified method of Barnard, EP 0 503 830 A1. In preparing the quinoline compound, cis-diamminedichloroplatinum(II) (1.5 g, 5.0 mmol) was suspended in 30 mL distilled water, and a quinoline solution was added with stirring. The quinoline solution was comprised of 1.25 mL (1.37 g, 10.6 mmol) quinoline dissolved in an equal volume of ethanol. This suspension was heated at 70°–80° C. until a transparent solution was obtained. This solution was treated with charcoal and filtered through Celite. Concentrated hydrochloric acid (6.25 mL) was added to the solution and refluxed overnight. The resulting suspension was cooled in an ice bath for two hours, filtered, washed with water, ethanol, and diethyl ether, and dried in air. If the product had been green, it would have been recrystallized from a minimum of hot dimethylformamide and 2N HCl. The yellow solid was filtered, washed with water, ethanol, and ether and dried in vacuo with heat overnight; yield 70%.

The isoquinoline compound was prepared in a manner similar to the quinoline compound. Analysis, Calculated for L=quinoline, isoquinoline: C$_9$H$_{10}$N$_2$Cl$_2$Pt; C, 26.12; H, 2.43; N, 6.80; Cl, 17.23. Found for L=quinoline: C, 26.42; H, 2.19; N, 6.68;, Cl, 17.37. Found for L=isoquinoline: C, 26.44; H, 2.29; N, 6.65; Cl, 17.25.

EXAMPLE 3

Preparation of Trans-[PtCl$_2$(4-picoline)$_2$]

The following reaction scheme was used:

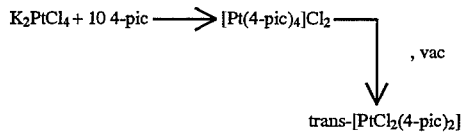

The complex was prepared by a modified method of Van Beusichem, M., and Farrell, N. "Activation of the Trans Geometry in Platinum Antitumor Complexes. Synthesis, Characterization, and Biological Activity of Complexes with the Planar Ligands Pyridine, N-Methylimidazole, Thiazole, and Quinoline. Crystal and Molecular Structure of trans-Dichlorobis(thiazole)platinum(II)." *Inorg. Chem.*, (1992), 31, 634–639.

To a solution of (5.0 g, 12.0 mmol) K$_2$PtCl$_4$ dissolved in 50 mL distilled water, a solution of (11.7 mL, 11.2 g, 120 mmol) 4-picoline dissolved in 12.5 mL water, was added with stirring. The solution was stirred overnight with gentle heating. The resulting suspension was filtered and washed with acetone and ether. The white solid was placed in a 500 mL round bottom flask and heated at 100° C. under vacuum for three days with occasional mixing to give a yellow solid. The product was then stirred with water to remove residual [Pt(4-pic)$_4$]Cl$_2$, filtered, washed with water, acetone and ether, and dried in vacuo with heat; yield 83%.

EXAMPLE 4

Preparation of Trans-[Pt(NO$_3$)$_2$L$_2$]; wherein L= Picoline

The following reaction scheme was used:

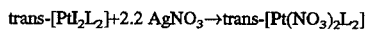

The complex was prepared by a modified method of Johnson et al. See Souchard, J. -P., Wimmer, F., Ha, T. T. B., Johnson, N. P. "A Rapid Method for the Synthesis of Water-soluble Platinum(II) Amine and Pyridine Complexes." *J. Chem. Soc. Dalton Trans.*, (1990), 307–310.

Finely powdered silver nitrate (2.2 equivalents) was added to a solution of trans-[PtI$_2$L$_2$] in acetone (1.0 mmol in 80 mL). This suspension was stirred in the dark for eight days then filtered through Celite to remove AgI. The filtrate was heated with charcoal and again filtered through Celite. To dissolve the precipitate that forms when filtering, the suspension was heated gently. The solution was allowed to cool slowly to room temperature resulting in the formation of small crystals. (The 4-picoline complex gave cream colored crystals.) The solution may be refrigerated to complete crystallization. The crystals were filtered, washed with ether and dried in air; yield 53%.

Alternate method: Instead of stirring the trans-[PtI$_2$L$_2$]/ AgNO$_3$ suspension at room temperature for eight days, it was heated gently overnight. AgI was filtered from the acetone solution through Celite, and the filtrate was evaporated to dryness to give a white powder; yield 82%.

EXAMPLE 5

Preparation of Trans-[PtCl(Me$_2$SO)(NH$_3$)L](NO$_2$); wherein L=Quinoline and Isoquinoline The following reaction scheme was used:

trans-[PtCl$_2$(NH$_3$)L] + Me$_2$SO +

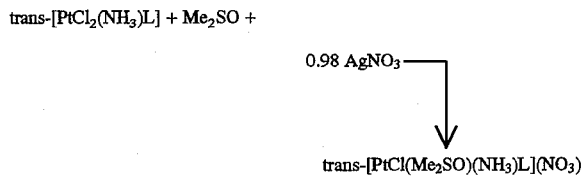

Dimethyl sulfoxide (709 μL, 0.0781 g, 1.0 mmol) was added to a suspension of trans-[PtCl$_2$(NH$_3$)L] in 25 mL methanol. A solution of silver nitrate (0.167 g, 0.98 mmol) dissolved in 12 mL methanol was added dropwise with stirring. This solution was gently refluxed overnight in the dark. Silver chloride was filtered from the solution through Celite. The methanol was evaporated off to give an oil which was stirred with ether for several hours and then evaporated. A small amount of methanol was added to dissolve the oil, and ether was again added and the mixture stirred. This was repeated several more times until a white solid and a yellow oil formed when the solvents were evaporated off. Methanol was added to dissolve the oil. The white solid was filtered, washed with ether and dried in vacuo. The product was recrystallized from hot methanol; yield 68%. Analysis, Calculated for C$_{11}$H$_{16}$N$_3$ClO$_4$Pt: C, 25.56; H, 3.10; N, 8.13; Cl, 6.87. Found for L=quinoline: C, 25.72; H, 2.74; N, 7.92; Cl 6.97. Found for L=isoquinoline: C, 25.32; H, 2.75; N, 7.82; Cl, 6.74.

EXAMPLE 6

Preparation of Trans-[PtCl$_2$(OH)$_2$(NH$_3$)L]; wherein L=Quinoline and Isoquinoline The following reaction scheme was used:

trans-[PtCl$_2$(NH$_3$)L] + xs 30% H$_2$O$_2$

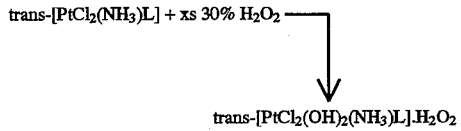

These complexes were prepared by a modified method of Hoeschele, J. D., Ferren, L. A., Roberts, J. A., and Whitfield, L. R. "Biodistribution and Pharmacokinetics of 195 mPt-Labeled cis-Dichloro-trans-Dihydroxo-bis(Isopropylamine) Platinum(IV), CHIP, In the Normal Female Fischer 344 Rat." In Hacker, M. P., Douple, E. B., Krakoff, I. H., Eds. Platinum Coordination Complexes in Cancer Chemotherapy, Martinus Nijhoff, Boston, Mass., 1984.

A suspension of trans-[PtCl$_2$(NH$_3$)L] (1.0 g) in 20 mL 30% H$_2$O$_2$ was refluxed for two hours and allowed to cool to room temperature. The resulting suspension was filtered, washed with ethanol and ether, and dried in vacuo; yield 70%. Analysis, Calculated for L=quinoline, isoquinoline: C$_9$H$_{12}$N$_2$Cl$_2$O$_2$Pt.H$_2$O$_2$: C, 22.50; H, 2.92; N, 5.83; Cl, 14.79. Found for L=quinoline: C, 22.57; H, 2.57; N, 5.51; Cl, 14.81. Found for L=isoquinoline: C, 22.86; H, 2.51; N, 5.45; Cl, 15.78; small amount of sample.

EXAMPLE 7

Preparation of Mer, trans-[PtCl$_3$(OH)(NH$_3$)(quinoline)

The following reaction scheme was used:

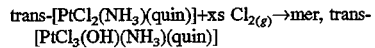

NH$_3$ remains trans to the quinoline group.

Chlorine gas is generated by adding concentrated HCl to solid KMnO$_4$ dropwise, and is then bubbled through a suspension of trans-PtCl$_2$(NH$_3$)(quin)] (300 mg) in 5.0 mL water for three to ten minutes. The suspension is then filtered, washed with water, ethanol, and ether, and dried in vacuo without heat. Completeness of the reaction can be monitored by $^1$H NMR of the produce in DMF-d$_7$. If the Pt(II) complex is still present, the solid may be resuspended in water and chlorine bubbled through again.

The results of the NMR elemental analysis of the quinoline complex are set forth in the table below:

| Calculated for [PtCl$_3$(OH)(NH$_3$)(quin)] | Found |
| --- | --- |
| 23.25 | 23.63 |
| 2.37 | 2.02 |
| 6.03 | 5.85 |
| 22.93 | 23.02 |

IR spectrum confirms the presence of the bound hydroxide.

EXAMPLE 8

Preparation of Trans-[PtCl$_4$(NH$_3$)L]; wherein L= Quinoline and Isoquinoline

The following reaction scheme was used:

Suspend 1.86 g (4.17 mmol) trans-[PtCl$_2$(OH)$_2$(NH$_3$) (quin)] in 150 mL concentrated HCl. Heat gently (30°-35° C.) with stirring overnight. Cool in an ice bath and filter. Wash with water, a small amount of ethanol and ether. Dry in vacuo without heat. Let the filtrate stand and a second crop precipitates. Filter and wash as before. The product may be purified by running it down a silica column. Dissolve the crude product in DMF (70 mg/mL); mobile phase: Benzene/Acetone/Glacial acetic acid, 4:2:1. The product is the first band to elute off the column; yield 35%. Analysis, Calculated for C$_9$H$_{10}$N$_2$Cl$_4$Pt: % C, 22.36; % H, 2.07; % N, 5.80; % Cl, 29.40. Found: % C, 22.31; % H, 2.12; % N, 5.69; % Cl, 28.58.

The isoquinoline compound was prepared in a manner similar to the quinoline compound.

EXAMPLE 9

Preparation of Trans-[PtCl$_2$(OOCCH$_3$)$_2$(NH$_3$)(quin)]

The following reaction scheme was used:

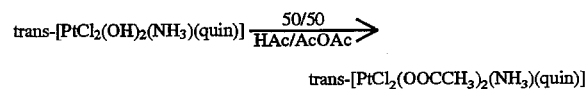

Suspend trans-[PtCl$_2$(OH)$_2$(NH$_3$)(quin)] in a 50/50 glacial acetic acid/acetic anhydride solution (0.5 mmol/2.0 mL total solution volume). Stir at room temperature for 48 hours. Filter off yellow solid that has formed. To recrystallize dissolve complex in a minimum of warm dimethylformamide. Add ethyl ether (10×) and let stand in freezer overnight to precipitate product. Filter off precipitate and wash with $Et_2O$. Dry in vacuo without heat; yield 30–40%. Analysis. Calculated for: % C, 29.43; % H, 3.02; % N, 5.28; % Cl, 13.40. Found: % C, 29.66; % H, 3.21; % N, 5.28; % Cl, 13.19.

Purity can be checked by TLC (as well as NMR and IR). The stationary phase used was silica on aluminum support. The mobile phase was a mixture of benzene, acetone, and glacial acetic acid in the ratio of 4:2:1. $R_1$=0.63.

EXAMPLE 10

Preparation of Trans-[$PtCl_2(NH_3)$(thiazole)]

cis-[$PtCl_2(NH_3)_2$] (1.5 g; 5.0 mmol) was suspended in water (30 mL) in a 100 mL round-bottomed flask. Thiazole (0.78 mL; 11 mmol) was added to the solution and the resulting mixture heated at 60°–70° C., with stirring, until no more solid remained and the solution had become a pale yellow color. Activated charcoal was then added and the solution filtered through celite. Concentrated HCl (6.25 mL) was added to the filtrate and the solution gently refluxed for four hours, during which time, a small quantity of yellow solid had precipitated. Heating was ceased, the volume reduced to approximately half, and the reaction mixture cooled in an ice-bath for 30 minutes. The resulting solid was washed with ice-cold water (2×5 mL), cold ethanol (2×5 mL) and diethylether (2'10 mL).

The solid was recrystallized from the minimum quantity of boiling water needed to remove any [Pt(thiazole)$_4$][$PtCl_4$] which had formed. The "Magnus"-type salt is insoluble in water and was filtered off. Trans-[$PtCl_2(NH_3)$(thiazole)] was obtained by evaporating the aqueous filtrate to a very small volume, cooling in an ice-bath, filtering, and washing the solid with cold ethanol (2×5 mL) and diethylether (2×10 mL). The complex was then dried overnight in an evacuated heating pistol over boiling acetone.

Yield: 60–70% Microanalysis for $PtCl_2SC_3H_6N_2$ (Calc (Found)): % C, 9.79 (9.93); % N, 7.61 (7.33); % H, 1.64 (1.51); % Cl, 19.26 (19.25). $^1H$ NMR Data:

For trans-[$PtCl_2(NH_3)$(thiazole)] (1)

Solvent: $d_7$-dmf. $\delta(H_2)$=9.60; $\delta(H_4)$=8.26; $\delta(H_5)$=7.97; $\delta(NH_3)$=4.22 Solvent: $CD_3CN$. $\delta(H_2)$=9.35; $\delta(H_4)$=8.20; $\delta(H_5)$=7.61; $\delta(NH_3)$=3.30 Solvent: $d_6$-acetone. $\delta(H_2)$=9.53; $\delta(H_4)$=8.28; $\delta(H_5)$=7.83; $\delta(NH_3)$=3.82

For [Pt(thiazole)$_4$][$PtCl_4$](II)

Solvent: $d_7$-dmf. $\delta(H_2)$=9.69; $\delta(H_4)$=8.31; $\delta(H_5)$=8.05 IR Data:

For (I): $\sqrt{}$ (Pt-Cl)=325 $cm^{-1}$
For (II): $\sqrt{}$ (Pt-Cl)=335 $cm^{-1}$

EXAMPLE 11

Preparation of Trans-[$PtCl_2(NH_3)$(benzothiazole)]

cis-[$PtCl_2(NH_3)_2$] (1.0 g; 3.3 mmol) was suspended in water (75 mL) in a 250 mL round-bottomed flask. Benzothiazole (0.91 mL; 8.3 mmol; 2.5 mole equivalents) was added and the solution heated, with stirring, at 70° C. until there was no starting complex undissolved. (N.B. if only a small amount of cis-[$PtCl_2(NH_3)_2$] was remaining and the solution beginning to discolor, the reaction was treated as if all cis-[$PtCl_2(NH_3)_2$] had dissolved.) Activated charcoal was then added and the solution was stirred for an additional 10 minutes. This mixture was then filtered through a celite pad. Concentrated HCl (15 mL) was added to the filtrate and the solution refluxed gently for 3 hours. During this time, a small quantity of pale yellow solid had precipitated. The solution was then cooled in an ice bath for 60 minutes and the resulting solid filtered off and washed with ice-cold ethanol (2×5 mL) and diethylether (2×10 mL).

The crude product can be recrystallized by dissolving the solid in the minimum amount of boiling acetone (approximately 0.6 g in 100 mL). The solution is then treated with charcoal, filtered through a celite pad and the filtrate evaporated to a small volume. This solution was allowed to sit at 4° C. for 6 hours. The resulting solid was filtered and washed with diethylether (2×10 mL) and dried in an evacuated drying pistol over boiling acetone.

Yield: 60% $^1H$ NMR: Solvent=$d_7$-dmf $\delta(H_2)$=10.0; $\delta$(benzo-protons)=9.09, 8.42, 7.90, 7.78. Microanalysis (Calc/Found): % Cl, 16.95 (16.95); % C, 20.10 (20.18); % H, 1.93 (1.90); % N, 6.70 (6.61).

EXAMPLE 12

Preparation of Trans-$PtCl_4(NH_3)$(thiazole)]

trans-[$PtCl_2(NH_3)$(thiazole)] (1 g; mmol) was suspended in water (30 mL) at room temperature. Chlorine gas, generated by reacting concentrated HCl with $KMnO_4$, was bubbled through the suspension for 10 minutes. The mixture was capped and allowed to stir, at room temperature, for an additional 20 minutes. $Cl_2$ was again bubbled through the mixture for 5 minutes, with stirring, after which the suspension was capped and allowed to stir at room temperature for 25 minutes. The resulting mixture was evaporated to two-thirds volume, cooled in an ice-bath for 30 minutes and the resulting solid filtered and washed with ethanol (2×5 mL) and diethylether (2×10 mL).

NMR shows the solid obtained is always a mixture of mer, trans-[$PtCl_3(OH)(NH_3)$(thiazole)] and trans-[$PtCl_4(NH_3)$(thiazole)]. To obtain pure trans, trans, trans-[$PtCl_4(NH_3)$(thiazole)], a Soxhlet extraction using methanol or acetonitrile is performed on the solid mixture. 50 mL of solvent is used per gram of solid and the extraction performed for 8 hours. After this time, the solvent is collected and evaporated to dryness. If the resulting complex is still impure, the extraction may be performed a second time. The complex mer, trans-[$PtCl_3(OH)(NH_3)$(thiazole)] is slightly more soluble in acetonitrile than in methanol. Hence, remaining contamination is more likely if acetonitrile is used as the extracting solvent. The compound trans-[$PtCl_4(R'R''SO)$ quinoline], wherein R' is methyl and R'' is methyl, benzyl or phenyl can be made in the same manner as above.

Yield: 25–30% Microanalysis for $PtCl_4SC_3H_6N_2$ (Calc (Found)): % C, 8.21 (8.32); % H, 1.38 (1.27); % N, 6.38 (6.37); % Cl, 32.30 (32.18). $^1H$ NMR Data: Solvent: $d_7$-dmf. $\delta(H_2)$=9.89; $\delta(H_4)$=8.43; $\delta(H_5)$=8.21; $\delta(NH_3)$=6.62 Solvent: $d_6$-acetone. $\delta(H_2)$=9.77; $\delta(H_4)$=8.43; $\delta(H_5)$=8.07; $\delta(NH_3)$=6.00.

EXAMPLE 13

Preparation of Trans, trans, trans-[$PtCl_2(OH)_2(NH_3)$(thiazole)]

trans-[$PtCl_2(NH_3)$(thiazole)] (0.5 g; mmol) was suspended in fresh hydrogen peroxide (5 mL) and stirred, at room temperature, for 90 minutes. After this time, the small amount of remaining starting material was filtered off. Ethanol (10 mL) was added to the filtrate followed by diethylether (50 mL), precipitating a yellow solid. This mixture was cooled in an ice-bath for approximately 2 hours after which the solid was filtered off and washed with a small quantity of ice-cold ethanol (1×5 mL) and portions of diethylether (3×5 mL).

Yield: 0.37 g; 67%. Microanalysis for $PtCl_2O_2C_3H_8N_2S$ (Calc (Found)): % C, 8.96 (8.79); % H, 2.00 (2.07); % N, 6.97 (6.69); % Cl, 17.63 (15.98). $^1$H NMR Data: Solvent: $d_6$-dmso. $\delta(H_2)$=9.66; $\delta(H_4)$=8.33; $\delta(H_5)$=8.04; $\delta(NH_3)$= 5.58 Solvent: $d_4$-methanol. $\delta(H_2)$=9.50; $\delta(H_4)$=8.28; $\delta(H_5)$ =7.84 Solvent: $D_2O$. $\delta(H_2)$=9.51; $\delta(H_4)$=8.27; $\delta(H_5)$=7.92 IR Data: $\nu(O—H)$=3510 cm$^{-1}$

EXAMPLE 14

Preparation of Trans, trans, trans-[$PtCl_2(OH)_2(NH_3)$ (benzothiazole)].$H_2O_2$ trans-[$PtCl_2(NH_3)$(benzothiazole)] (0.25 g; 0.60 mmol) was suspended in 30% hydrogen peroxide solution (7.5 mL) and heated at 70° C. until all solids present had dissolved. After this time, the solution was cooled in an ice bath for 15 minutes. A small quantity of ethanol (2 mL) was carefully added to the solution immediately followed by the addition of diethylether (25 mL). A yellow solid precipitated. The mixture was allowed to stand at 0° C. for an additional 30 minutes before the solid was collected by filtration.

Yield: 0.16 g: 55%. $^1$H NMR: Solvent=$d_7$-dmf $\delta(H_2)$= 9.72; $\delta(H_5)$=8.10; $\delta(H_6+H_7)$=7.60; $\delta(H_8)$=8.76. Microanalysis (Calc (Found)): % Cl, 14.58 (14.55); % C, 17.29 (17.24); % H, 2.49 (2.42); % N, 5.76 (5.67).

While the invention has been described in terms of various preferred embodiments, one skilled in the art will appreciate that various modifications, substitutions, omissions, and changes may be made without departing from the spirit thereof. Accordingly, it is intended that the scope of the present invention be limited solely by the scope of the following claims.

I claim:

1. A trans platinum(IV) complex of the formula

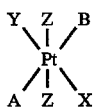

(I)

wherein the A and B ligands are trans with respect to the platinum atom, and wherein A is a ligand selected from the group consisting of quinoline, isoquinoline, isothiazole, thiazole, benzisotriazole, indole, pyrazole, 1, 2, 3-triazole, pyrazine, isoindole, indoline, cinnoline, quinazoline, 1,8-naphthyridine, and acridine, and B is a ligand selected from the group consisting of quinoline, isoquinoline, isothiazole, thiazole, benzisotriazole, indole, pyrazole, 1,2,3-triazole, pyrazine, isoindole, indoline, cinnoline, quinazoline, 1,8-naphthyridine, acridine, and ammonia, or is a primary amine, selected from the group consisting of alkyl amines of the formula $NH_2—R_1$ where $R_1$ is a linear or branched $C_1–C_8$ alkyl or a $C_3–C_6$ cycloalkyl or a secondary amine of the formula $NH(R_1)_2$ where $R_1$ is H or a linear or branched $C_1–C_8$ alkyl, X and Y, which are the same or different, are an anionic ligand comprising halide, sulfate, nitrate, hydroxy, carboxylate, or pseudohalogen; Z is halide, hydroxyl, or —OCO—R, —OC(O)—OR, or —OSO$_2$—R, wherein R is H, linear or branched $C_1–C_8$ alkyl, $C_3–C_6$ cycloalkyl, phenyl, substituted phenyl, or $C_7–C_{10}$ aralkyl; or is a sulphoxide group of formula R'R"SO, wherein R' is linear or branched $C_1–C_8$ alkyl and R" is selected from the group consisting of linear and branched $C_1–C_8$ alkyl; phenyl unsubstituted or substituted by one or two halogens, mono and dimethoxy substituted phenyl; and $C_7–C_{10}$ aralkyl.

2. The trans platinum(IV) complex of claim 1, wherein Z is R'R"SO and R" is a $C_7–C_{10}$ aralkyl of benzyl, phenylethyl or phenylpropyl and R' is linear or branched $C_1–C_8$ alkyl.

3. The trans platinum(IV) complex of claim 1, wherein Z is R'R"SO and R' is methyl, R" is methyl, benzyl or phenyl.

4. The trans platinum(IV) complex of claim 1, wherein the primary amine has the formula $NH_2—R_1$ and $R_1$ is methyl, ethyl, n-propyl, isopropyl, n-butyl, sec-butyl, tert-butyl, n-pentyl, n-hexyl, or n-octyl.

5. The trans platinum (IV) complex of claim 1, wherein the $C_3–C_6$ cycloalkyl is cyclopropyl, cyclobutyl, cyclopentyl, or cyclohexyl.

6. The trans platinum(IV) complex of claim 1, wherein the secondary amine has the formula $NH(R_1)_2$ and $R_1$ is linear or branched $C_1–C_8$ alkyl.

7. The trans platinum(IV) complex of claim 6, wherein the linear or branched $C_1–C_8$ alkyl is methyl, ethyl, n-propyl, isopropyl, n-butyl, sec-butyl, tert-butyl, n-pentyl, n-hexyl, or n-octyl.

8. The trans platinum(IV) complex of claim 1, wherein Z is —OCO—R, —OC(O)OR, or —OSO$_2$—R and R is a linear or branched $C_1–C_8$ alkyl of methyl, ethyl, n-propyl, isopropyl, n-butyl, sec-butyl, tert-butyl, n-pentyl, n-hexyl, or n-octyl.

9. The trans platinum(IV) complex of claim 1, wherein Z is —OCO—R, —OC(O)OR, or —OSO$_2$—R and R is a $C_3–C_6$ cycloalkyl of cyclopropyl, cyclobutyl, cyclopentyl, or cyclohexyl.

10. The trans platinum(IV) complex of claim 1, wherein Z is —OCO—R, —OC(O)OR, or —OSO$_2$—R and R is a substituted phenyl of ortho, meta and para tolyl, mono or di chloride, bromide or fluoride substituted phenyl, or methoxy or dimethoxy substituted phenyl.

11. The trans platinum(IV) complex of claim 1, wherein Z is —OCO—R, —OC(O)OR, or —OSO$_2$—R and R is a $C_7–C_{10}$ aralkyl of phenylmethyl, phenylethyl, or phenylpropyl.

12. The trans platinum(IV) complex of claim 1, wherein the pseudohalogen is SCN$^-$, CN$^-$, or NO$_3^-$.

13. The trans platinum(IV) complex of claim 1, wherein Z is R'R"SO and R" is an unsubstituted or substituted phenyl of mono or dichloride, bromide or fluoride substituted phenyl, or methoxy or dimethoxy substituted phenyl and R' is linear or branched $C_1–C_8$ alkyl.

14. The trans platinum(IV) complex of claim 1, which comprises trans, trans, trans-[$PtCl_2(OH)_2(NH_3)L$], wherein L=quinoline, isoquinoline, and thiazole;

mer, trans-[$PtCl_3(OH)(NH_3)$(quinoline)];

trans-[$PtCl_4(NH_3)L$], wherein L=quinoline, isoquinoline, and thiazole;

trans, trans, trans-[$PtCl_2(OOCCH_3)_2(NH_3)$(quinoline)]; or trans-[$PtCl_4(R'R"SO)$quinoline], wherein R' is methyl and R" is methyl, benzyl or phenyl.

15. A pharmaceutical composition comprising a tumor-inhibiting effective amount of a complex according to claim 1, in a pharmaceutically acceptable carrier.

16. A method of inhibiting tumor growth in a mammal, comprising administering a tumor-inhibiting effective amount of a complex according to claim 1.

17. The trans platinum(IV) complex of claim 1, wherein Z is R'R"SO and R', R" are a linear or branched $C_1–C_8$ alkyl of methyl, ethyl, n-propyl, isopropyl, n-butyl, or tert-butyl.

* * * * *